United States Patent
Shrestha et al.

(10) Patent No.: US 9,482,610 B2
(45) Date of Patent: Nov. 1, 2016

(54) TECHNIQUES FOR MATCHING SPECTRA

(71) Applicant: Applied Materials, Inc., Santa Clara, CA (US)

(72) Inventors: Kiran Lall Shrestha, San Jose, CA (US); Boguslaw A. Swedek, Cupertino, CA (US); Jeffrey Drue David, San Jose, CA (US); Harry Q. Lee, Los Altos, CA (US)

(73) Assignee: Applied Materials, Inc., Santa Clara, CA (US)

( * ) Notice: Subject to any disclaimer, the term of this patent is extended or adjusted under 35 U.S.C. 154(b) by 988 days.

(21) Appl. No.: 13/674,667

(22) Filed: Nov. 12, 2012

(65) Prior Publication Data

US 2014/0134758 A1    May 15, 2014

(51) Int. Cl.
| | |
|---|---|
| *G01R 23/16* | (2006.01) |
| *G01N 21/47* | (2006.01) |
| *B24B 49/12* | (2006.01) |
| *B24B 37/005* | (2012.01) |
| *H01L 21/66* | (2006.01) |

(52) U.S. Cl.
CPC .............. *G01N 21/47* (2013.01); *B24B 37/005* (2013.01); *B24B 49/12* (2013.01); *H01L 22/12* (2013.01); *H01L 22/20* (2013.01)

(58) Field of Classification Search
CPC ..... H01L 22/12; H01L 22/20; B24B 37/005; B24B 49/12; G01N 21/47
USPC .......................................................... 702/189
See application file for complete search history.

(56) References Cited

U.S. PATENT DOCUMENTS

| | | | |
|---|---|---|---|
| 2007/0042675 A1 | 2/2007 | Benvegnu et al. | |
| 2009/0201309 A1* | 8/2009 | Demos ....................... | G01J 3/02 345/589 |
| 2010/0056023 A1* | 3/2010 | David ................... | B24B 37/005 451/5 |
| 2010/0114532 A1 | 5/2010 | David et al. | |
| 2010/0217430 A1 | 8/2010 | David et al. | |
| 2011/0256805 A1* | 10/2011 | David ................... | B24B 37/013 451/5 |
| 2011/0269377 A1* | 11/2011 | Qian ..................... | B24B 37/013 451/5 |
| 2012/0034845 A1 | 2/2012 | Hu et al. | |
| 2012/0096006 A1* | 4/2012 | David ..................... | H01L 22/12 707/741 |
| 2012/0276814 A1* | 11/2012 | Zhang ................... | B24B 37/013 451/5 |
| 2012/0278028 A1 | 11/2012 | David et al. | |

* cited by examiner

*Primary Examiner* — Paul D Lee
(74) *Attorney, Agent, or Firm* — Fish & Richardson P.C.

(57) ABSTRACT

A method of controlling processing of a substrate includes measuring a spectrum reflected from the substrate, for each partition of a plurality of partitions of the measured spectrum, computing a partition value based on the measured spectrum within the partition to generate a plurality of partition values, for each reference spectrum signature of a plurality of reference spectrum signatures, determining a membership function for each partition, for each partition, computing a membership value based on the membership function for the partition and the partition value for the partition to generate a plurality of groups of membership values with each group of the plurality of groups associated with a reference spectrum signature, selecting a best matching reference spectrum signature from the plurality of reference spectra signatures based on the plurality of groups of membership values, and determining a characterizing value associated with the best matching reference spectrum signature.

21 Claims, 5 Drawing Sheets

TECHNIQUES FOR MATCHING SPECTRA

TECHNICAL FIELD

The present disclosure relates to spectrographic monitoring of a substrate.

BACKGROUND

An integrated circuit is typically formed on a substrate by the sequential deposition of conductive, semiconductive, or insulative layers on a silicon wafer. A variety of fabrication processes require planarization of a layer on the substrate. For example, for certain applications, e.g., polishing of a metal layer to form vias, plugs, and lines in the trenches of a patterned layer, an overlying layer is planarized until the top surface of a patterned layer is exposed. In other applications, e.g., planarization of a dielectric layer for photolithography, an overlying layer is polished until a desired thickness remains over the underlying layer.

Chemical mechanical polishing (CMP) is one accepted method of planarization. This planarization method typically requires that the substrate be mounted on a carrier or polishing head. The exposed surface of the substrate is typically placed against a rotating polishing pad. The carrier head provides a controllable load on the substrate to push it against the polishing pad. Abrasive polishing slurry is typically supplied to the surface of the polishing pad.

One problem in CMP is determining whether the polishing process is complete, i.e., whether a substrate layer has been planarized to a desired flatness or thickness, or when a desired amount of material has been removed. Variations in the slurry distribution, the polishing pad condition, the relative speed between the polishing pad and the substrate, and the load on the substrate can cause variations in the material removal rate. These variations, as well as variations in the initial thickness of the substrate layer, cause variations in the time needed to reach the polishing endpoint. Therefore, determining the polishing endpoint merely as a function of polishing time can lead to within-wafer non-uniformity (WIWNU) and wafer-to-wafer non-uniformity (WTWNU).

In some systems, a substrate is optically monitored in-situ during polishing, e.g., through a window in the polishing pad. However, existing optical monitoring techniques may not satisfy increasing demands of semiconductor device manufacturers.

SUMMARY

In some in-situ monitoring processes, a spectrum is measured from a substrate. The spectrum is compared to a plurality of reference spectra from a library, and the best matching reference spectrum is identified. One technique for identifying the best matching reference spectrum is to identify the spectrum with the least difference using a sum of squares algorithm. However, the sum of squares technique is computationally heavy, e.g., requires a large number of calculations. The greater the computational load per reference spectrum, the fewer reference spectra that can be compared to the measured spectra while maintaining an acceptable real-time identification of the best matching reference spectrum. However, more efficient algorithms are possible for identifying a matching reference spectrum.

In one aspect, a method of controlling processing of a substrate includes processing a substrate, measuring a spectrum reflected from the substrate with a spectrographic monitoring system to generate a measured spectrum, for each partition of a plurality of partitions of the measured spectrum, computing a partition value based on the measured spectrum within the partition to generate a plurality of partition values, for each reference spectrum signature of a plurality of reference spectrum signatures, determining a membership function for each partition, for each partition, computing a membership value based on the membership function for the partition and the partition value for the partition to generate a plurality of groups of membership values with each group of the plurality of groups associated with a reference spectrum signature, selecting a best matching reference spectrum signature from the plurality of reference spectra signatures based on the plurality of groups of membership values, determining a characterizing value associated with the best matching reference spectrum signature, and adjusting processing of the substrate or a subsequent substrate based on the characterizing value.

Implementations can include on or more of the following features. Computing the partition value may include computing an average value of the measured spectrum within the partition. Selecting a best matching reference spectrum signature may include, for each group, computing a total value of the membership values in the group to provide a plurality of totals values, and selecting a reference spectrum signature associated with a group having the largest total value of the plurality of total values. Selecting a best matching reference spectrum signature may include, for each group, determining a second-lowest value of the group of values to provide a plurality of second-lowest values, and selecting a reference spectrum signature associated with a group having the largest second-lowest value of the plurality of second-lowest values. Each reference spectrum signature may include a plurality of code values, and each code value of the plurality of code values may be associated with one of the plurality of partitions. Determining the membership function for each partition may include determining the code value in the reference spectrum signature associated with the partition, and determining the membership function associated with the code value. The plurality of membership functions may include a first triangular function having a first maximum value at a midpoint of a first intensity range and a second function having a second maximum value at a midpoint of a second intensity range, and the first triangular function and the second triangular function may have an equal value at a boundary between the first intensity range and the second intensity range. The plurality of reference spectrum signatures may be computed based on a plurality of reference spectra. Computing the plurality of reference spectrum signatures may include computing an average reference spectrum, and the average reference spectrum may be an average of the plurality of reference spectra. Boundary wavelengths between the partitions based on the average reference spectrum may be determined. Determining boundary wavelengths may include computing wavelengths of a plurality of inflection points in the average reference spectrum, and computing boundary wavelengths that are a fraction of a distance between adjacent inflection points. Boundary intensities between a plurality of intensity zones may be determined based on the average reference spectrum. A second partition value may be computed for each partition of the average reference spectrum, and determining boundary intensities may include selecting at least some of the second partition values. Determining boundary intensities may include calculating an average of the second partition values. For partition of each reference spectrum, a third partition value may be calculated based on the reference spectrum within the partition, and one of a plurality of unique code values may be selected based on comparing the third partition value to the intensity zones. Processing the substrate may include polishing the substrate. Measuring the spectrum may include monitoring the substrate with an in-situ spectrographic monitoring system. A sequence of measured spectra may be generated, the characterizing value for each measured spectrum of the sequence of measured spectra may be determined to generate a sequence of characterizing values, and a polishing endpoint or an adjustment to a polishing parameter may be computed based on the sequence of characterizing values.

In another aspect, a non-transitory computer program product, tangibly embodied in a machine readable storage device, includes instructions to carry out the method.

Implementations may optionally include one or more of the following advantages. Fewer computations are required per reference spectrum, permitting the best matching reference spectrum to be identified more quickly or permitting the number of reference spectra that are compared to be increased while maintaining an acceptable real-time identification. Reliability of the endpoint system to detect a desired polishing endpoint can be improved, and within-wafer and wafer-to-wafer thickness non-uniformity (WIWNU and WTWNU) can be reduced.

The details of one or more implementations are set forth in the accompanying drawings and the description below. Other aspects, features, and advantages will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
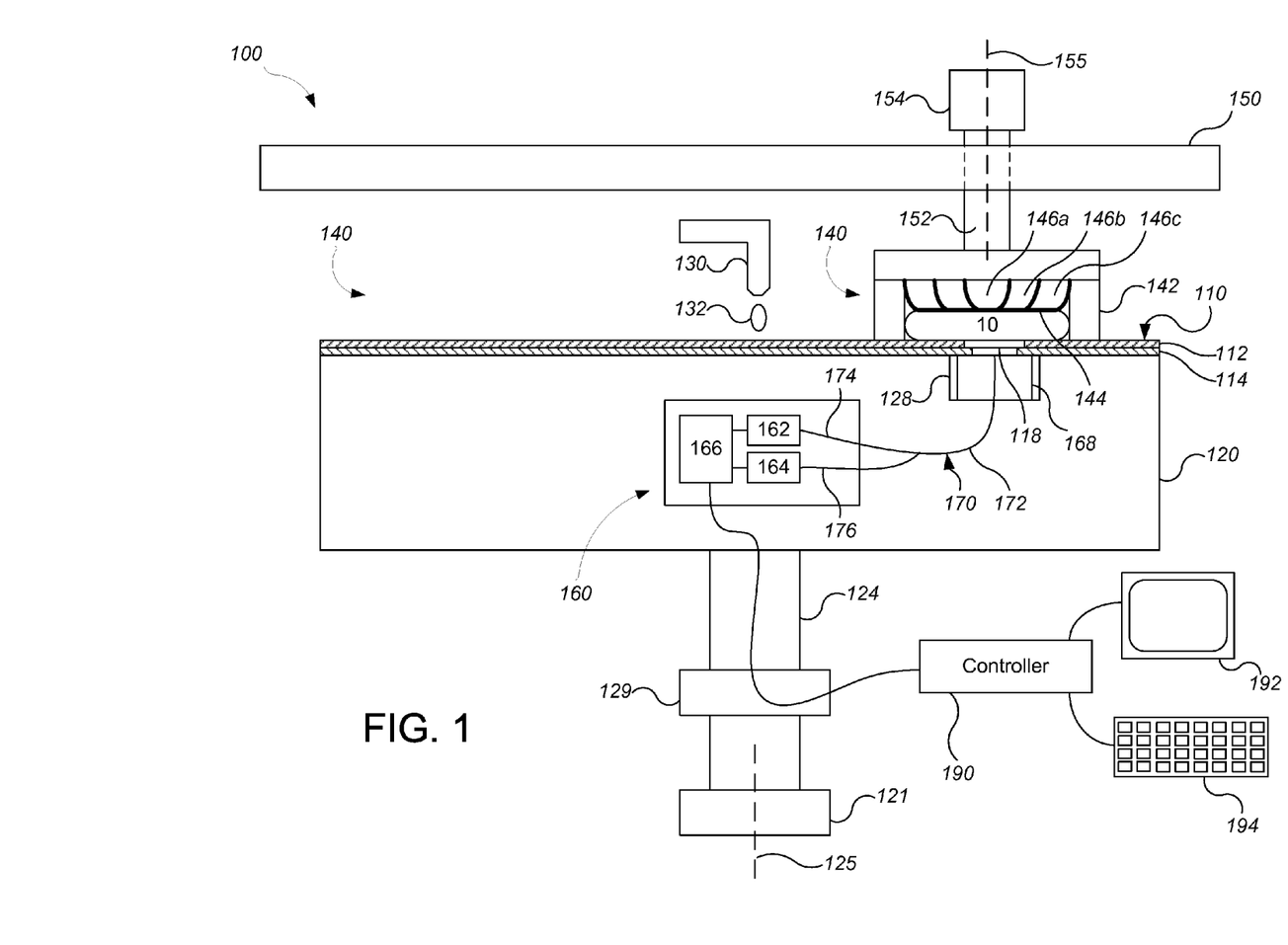
FIG. 1 illustrates a schematic cross-sectional view of an example of a polishing apparatus.

FIG. 1 illustrates an example of a polishing apparatus 100. The polishing apparatus 100 includes a rotatable disk-shaped platen 120 on which a polishing pad 110 is situated. The platen is operable to rotate about an axis 125. For example, a motor 121 can turn a drive shaft 124 to rotate the platen 120. The polishing pad 110 can be a two-layer polishing pad with an outer polishing layer 112 and a softer backing layer 114.

The polishing apparatus 100 can include a port 130 to dispense polishing liquid 132, such as slurry, onto the polishing pad 110 to the pad. The polishing apparatus can also include a polishing pad conditioner to abrade the polishing pad 110 to maintain the polishing pad 110 in a consistent abrasive state.

The polishing apparatus 100 includes at least one carrier head 140. The carrier head 140 is operable to hold a substrate 10 against the polishing pad 110. The carrier head 140 can have independent control of the polishing parameters, for example pressure, associated with each respective substrate.

In particular, the carrier head 140 can include a retaining ring 142 to retain the substrate 10 below a flexible membrane 144. The carrier head 140 also includes a plurality of independently controllable pressurizable chambers defined by the membrane, e.g., three chambers 146a-146c, which can apply independently controllable pressures to associated zones on the flexible membrane 144 and thus on the substrate 10. Although only three chambers are illustrated in FIG. 1 for ease of illustration, there could be one or two chambers, or four or more chambers, e.g., five chambers.

The carrier head 140 is suspended from a support structure 150, e.g., a carousel or a track, and is connected by a drive shaft 152 to a carrier head rotation motor 154 so that the carrier head can rotate about an axis 155. Optionally the carrier head 140 can oscillate laterally, e.g., on sliders on the carousel or track 150; or by rotational oscillation of the carousel itself. In operation, the platen is rotated about its central axis 125, and the carrier head is rotated about its central axis 155 and translated laterally across the top surface of the polishing pad.

While only one carrier head 140 is shown, more carrier heads can be provided to hold additional substrates so that the surface area of polishing pad 110 may be used efficiently.

The polishing apparatus also includes an in-situ monitoring system 160. The in-situ monitoring system generates a time-varying sequence of values that depend on the thickness of a layer on the substrate. The in-situ-monitoring system 160 is an optical monitoring system. In particular, the in-situ-monitoring system 160 measures a sequence of spectra of light reflected from a substrate during polishing. For each measured spectrum, a matching reference spectrum from a library of reference spectra is identified. Each reference spectrum in the library can have an associated characterizing value, e.g., a thickness value or an index value indicating the time or number of platen rotations at which the reference spectrum is expected to occur. By determining the associated characterizing value for each matching reference spectrum, a time-varying sequence of characterizing values can be generated. This technique is described in U.S. Patent Publication No. 2010-0217430, which is incorporated by reference.

An optical access through the polishing pad can be provided by including an aperture (i.e., a hole that runs through the pad) or a solid window 118. The solid window 118 can be secured to the polishing pad 110, e.g., as a plug that fills an aperture in the polishing pad, e.g., is molded to or adhesively secured to the polishing pad, although in some implementations the solid window can be supported on the platen 120 and project into an aperture in the polishing pad.

The optical monitoring system 160 can include a light source 162, a light detector 164, and circuitry 166 for sending and receiving signals between a remote controller 190, e.g., a computer, and the light source 162 and light detector 164. One or more optical fibers can be used to transmit the light from the light source 162 to the optical access in the polishing pad, and to transmit light reflected from the substrate 10 to the detector 164. For example, a bifurcated optical fiber 170 can be used to transmit the light from the light source 162 to the substrate 10 and back to the detector 164. The bifurcated optical fiber can include a trunk 172 positioned in proximity to the optical access, and two branches 174 and 176 connected to the light source 162 and detector 164, respectively.

In some implementations, the top surface of the platen can include a recess 128 into which is fit an optical head 168 that holds one end of the trunk 172 of the bifurcated fiber. The optical head 168 can include a mechanism to adjust the vertical distance between the top of the trunk 172 and the solid window 118.

The output of the circuitry 166 can be a digital electronic signal that passes through a rotary coupler 129, e.g., a slip ring, in the drive shaft 124 to the controller 190 for the optical monitoring system. Similarly, the light source can be turned on or off in response to control commands in digital electronic signals that pass from the controller 190 through the rotary coupler 129 to the optical monitoring system 160. Alternatively, the circuitry 166 could communicate with the controller 190 by a wireless signal.

Figures 2, 3:
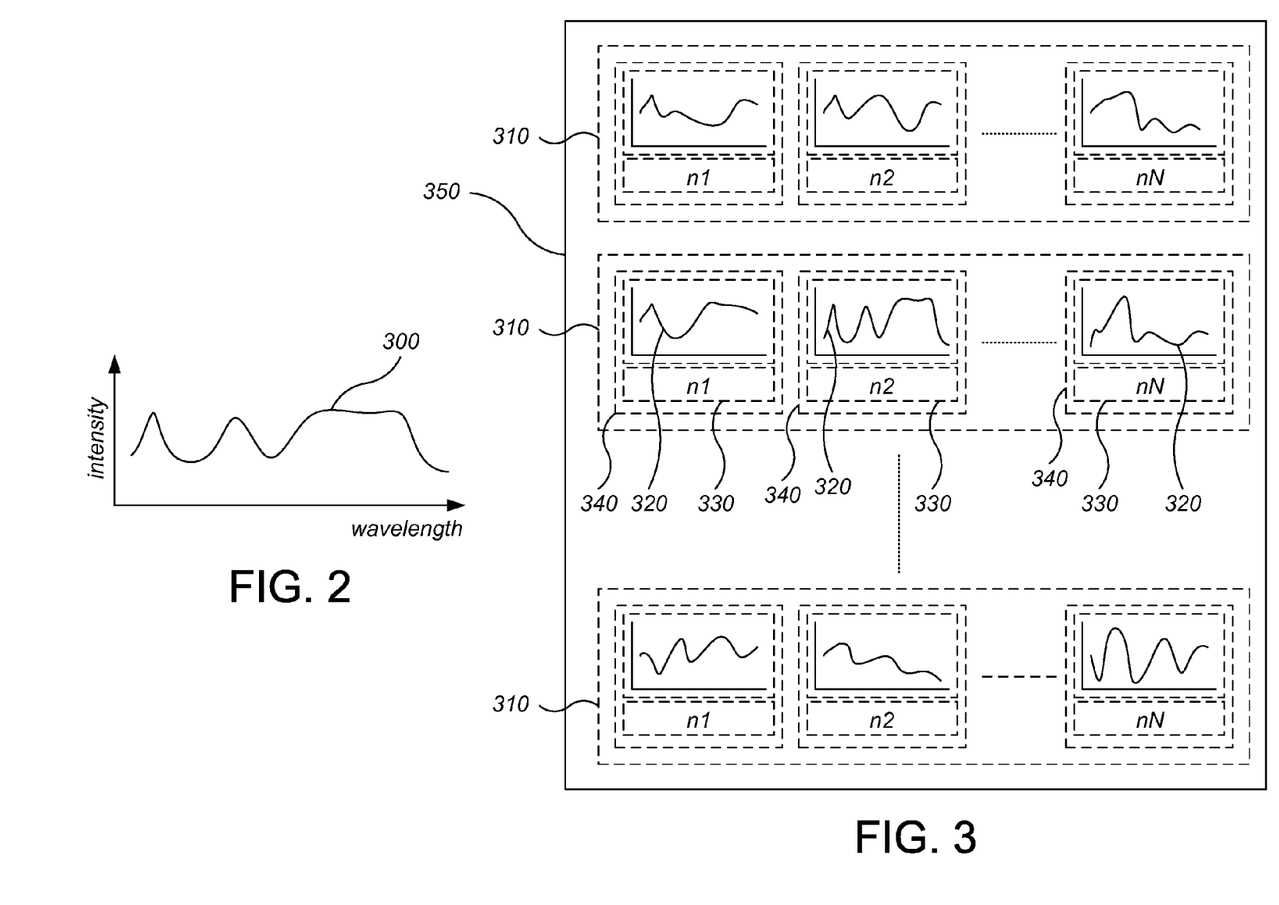
FIG. 2 illustrates a measured spectrum from the in-situ optical monitoring system.
FIG. 3 illustrates a library of reference spectra.

The light source 162 can be operable to emit ultraviolet (UV), visible or near-infrared (NIR) light. The light detector 164 can be a spectrometer. A spectrometer is an optical instrument for measuring intensity of light over a portion of the electromagnetic spectrum. A suitable spectrometer is a grating spectrometer. Typical output for a spectrometer is the intensity of the light as a function of wavelength (or frequency). FIG. 2 illustrates an example of a measured spectrum 300 with intensity as a function of wavelength.

As noted above, the light source 162 and light detector 164 can be connected to a computing device, e.g., the controller 190, operable to control their operation and receive their signals. The computing device can include a microprocessor situated near the polishing apparatus. For example, the computing device can be a programmable computer. With respect to control, the computing device can, for example, synchronize activation of the light source with the rotation of the platen 120.

The optical monitoring system 160 is configured to generate a sequence of measured spectra at a measurement frequency. In some implementations, the light source 162 and detector 164 of the in-situ monitoring system 160 are installed in and rotate with the platen 120. In this case, the measurement frequency can be once per rotation of the platen. It is possible for multiple spectra to be obtained as the optical access passes below the substrate 10, in which case one of the obtained spectra can be selected, or multiple obtained spectra can be combined, to provide the measured spectra.

In operation, the controller 190 can receive, for example, a signal that carries information describing a spectrum of the light received by the light detector for a particular flash of the light source or time frame of the detector. Thus, this spectrum is a spectrum measured in-situ during polishing.

Without being limited to any particular theory, the spectrum of light reflected from the substrate 10 evolves as polishing progresses (e.g., over multiple rotations of the platen, not during a single sweep across the substrate) due to changes in the thickness of the outermost layer, thus yielding a sequence of time-varying spectra. Moreover, particular spectra are exhibited by particular thicknesses of the layer stack.

The controller 190, e.g., the computing device, can be programmed to perform one monitoring techniques described above to generate the time-varying sequence of values. A display 192, e.g., a LED screen, and a user input device 194, e.g., a keyboard and/or a mouse, can be connected to the controller 190.

Referring to FIGS. 2 and 3, during polishing, a measured spectrum 300 can be compared to reference spectra 320 from a library 310 of reference spectra. The library 310 of reference spectra 320 can be stored in a database 350.

In some implementations, the database 350 can store a plurality of libraries 310 of reference spectra 320. In this case, each library of reference spectra can be a collection of reference spectra which represent substrates that share a property in common. However, the property shared in common in a single library may vary across multiple libraries of reference spectra. For example, two different libraries can include reference spectra that represent substrates with two different underlying thicknesses. For a given library of reference spectra, variations in the upper layer thickness, rather than other factors (such as differences in wafer pattern, underlying layer thickness, or layer composition), can be primarily responsible for the differences in the spectral intensities.

Reference spectra 320 for different libraries 310 can be generated by polishing multiple "set-up" substrates, e.g., substrates with different substrate properties (e.g., underlying layer thicknesses, or layer composition), and collecting spectra as discussed above. The spectra from a first set-up substrate can provide a first library, the spectra from a second set-up substrate can provide a second library, and the spectra from a third set-up substrate can provide a third library.

In general, each library 310 can include many reference spectra 320. For example, each library 310 can include one or more, e.g., exactly one, reference spectra for each platen rotation over the expected polishing time of the substrate.

In some implementations, each reference spectrum 320 is assigned a characterizing value 330, e.g., a thickness value or an index value. The index value can be a number of platen rotations or a time at which the associated spectrum would be expected to appear. The spectra can be indexed so that each spectrum in a particular library has a unique index value. The indexing can be implemented so that the index values are sequenced in an order in which the spectra were measured. An index value for the reference spectra in a library can be selected to change monotonically, e.g., increase or decrease, as polishing progresses. In particular, the index values of the reference spectra can be selected so that they form a linear function of time or number of platen rotations (assuming that the polishing rate follows that of the model or test substrate used to generate the reference spectra in the library). For example, the index value can be proportional, e.g., equal, to a number of platen rotations at which the reference spectra was measured for the test substrate or would appear in the optical model. Thus, each index value can be a whole number.

The reference spectra and their associated index values can be stored in a reference library. For example, each reference spectrum 320 and its associated index value 330 can be stored in a record 340 of database 350. The database 350 of reference libraries of reference spectra can be implemented in memory of the computing device of the polishing apparatus.

In some implementations, multiple potential libraries of potential reference spectra can be generated automatically from a lot of set-up substrates, and one of the potential libraries can be selected as the library 310 of reference spectra 320 to use for the endpoint detection and/or process control of a later device substrate.

As noted above, for each measured spectrum, a matching reference spectrum from a library 310 of reference spectra 320 is identified.

In order to perform the matching, each reference spectrum 320 can be assigned a code. Each reference spectrum 320 can have a unique code. Alternatively, some reference spectra can have the same code, in which case there will be multiple matches.

Figure 4:
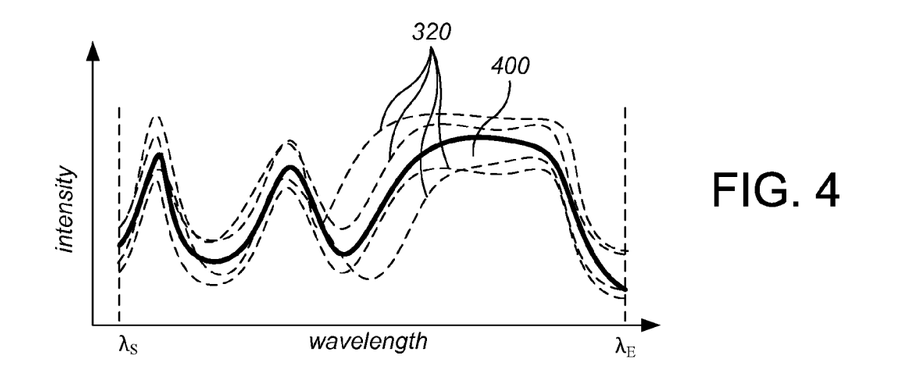
FIG. 4 illustrates computing an average reference spectrum from a library of reference spectra.

Initially, referring to FIG. 4, an average reference spectrum 400 is calculated. The average reference spectrum 400 is the average of the reference spectra 320 in a particular library 310. In the illustration in FIG. 4, the thick black trace is the average reference spectrum. The average reference spectrum can run from a starting wavelength $\lambda_S$ to an ending wavelength $\lambda_E$. Values for the starting wavelength $\lambda_S$ and the ending wavelength $\lambda_E$ may be stored in the controller.

Figure 5A:
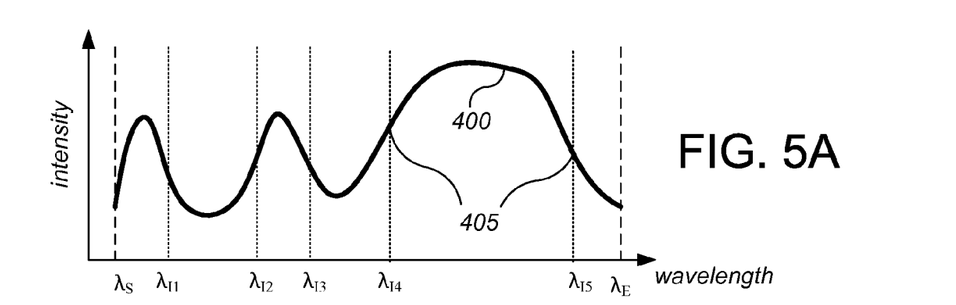
FIGS. 5A-5C illustrate partitioning the average reference spectrum.
Figure 5B:
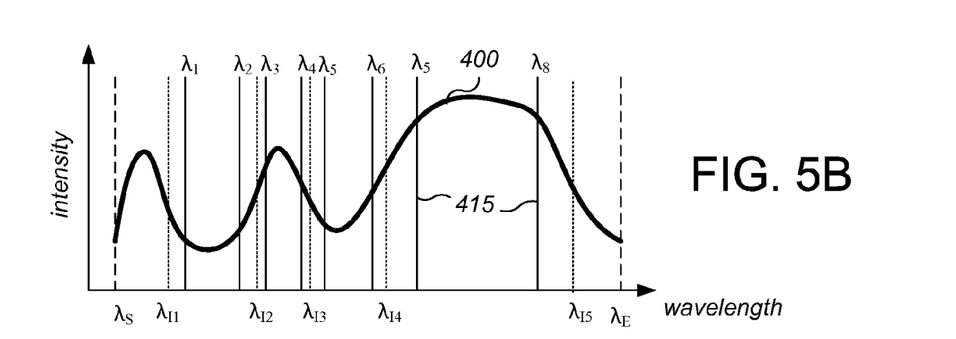
Figure 5C:
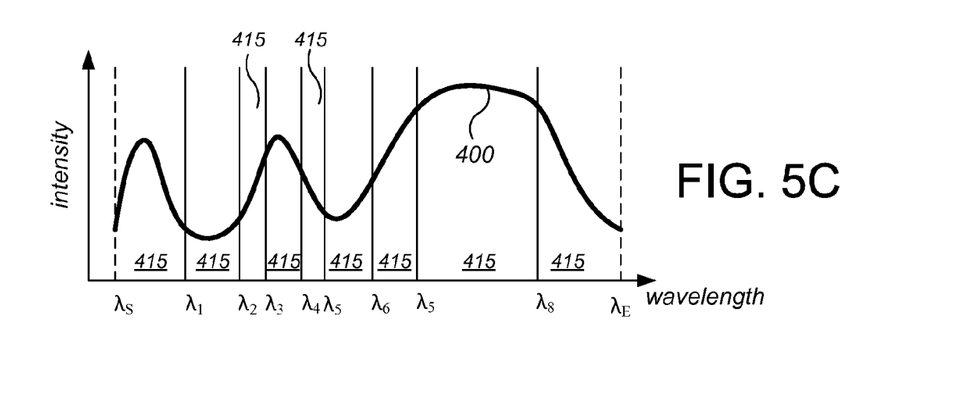

Referring to FIGS. 5A-5C, the average reference spectrum 400 is divided into a plurality of partitions 415. The partitions are non-overlapping wavelength ranges in the spectrum. In addition, the partitions can be sequential and contiguous. For example, a $1^{st}$ partition can run from the starting wavelength $\lambda_S$ of the average reference spectrum 400 to a first wavelength $\lambda_1$, a $2^{nd}$ partition can run from the first wavelength $\lambda_1$ to a second wavelength $\lambda_2$, etc. The last partition can extends to the to an ending wavelength $\lambda_E$. Thus, if there are N partitions, the $N^{th}$ partition can run from an $(N-1)^{th}$ wavelength $\lambda_{N-1}$ to the ending wavelength $\lambda_E$.

The controller calculates the wavelengths $\lambda_1, \lambda_2, \lambda_3 \ldots \lambda_{N-1}$ of the boundaries 410 between the partitions 410. The wavelengths of the boundaries are stored.

An example implementation to calculate the wavelengths of the boundaries of the partitions is as follows.

First the wavelength of each inflection point 405 in the average reference spectrum 400 is determined. In the example of FIG. 5A there are five inflection points at wavelengths wavelengths $\lambda_{I1}, \lambda_{I2}, \lambda_{I3}, \lambda_{I4}, \lambda_{I5}$, although there could be a different number of inflection points.

Turning to FIG. 5B, for each inflection point 405, the controller calculates a wavelength that that is a fraction, e.g., ⅛, of the distance to the neighboring inflexion point. For the first and last inflection points this wavelength is calculated only on one side of the infection point, but for the remaining inflection points this wavelength is calculated on both sides of the inflection point. Each of these wavelengths becomes a boundary of 410 between two partitions. For example, a first wavelength $\lambda_1$ can be calculated as $$\lambda_1 = \lambda_{I1} + (⅛)*(\lambda_{I2}-\lambda_{I1})$$

In the example of FIG. 5B-5C, this results in eight boundary wavelengths $\lambda_1, \lambda_2, \lambda_3, \lambda_4, \lambda_5, \lambda_6, \lambda_7$ and $\lambda_8$, which divide the spectrum into nine partitions 415.

Figure 6:
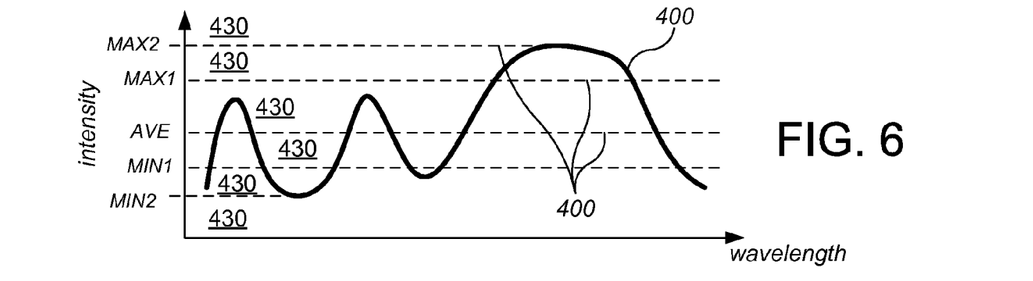
FIG. 6 illustrates determine intensity zones for the average reference spectrum.

Referring to FIG. 6, the controller breaks the spectrum into intensity zones 430. In one implementation, there are six intensity zones 430. The controller calculates the intensity values of the boundaries 435 between the zones 430. The intensity values of the boundaries 435 are stored.

An example implementation to calculate the intensity values of boundaries of the zones is as follows.

For each partition 410, a partition value is calculated based on the portion of the average spectrum within the partition. For example, for each partition 410 (see FIG. 5C), the controller calculates the average value of the spectrum within that partition, thus generating a group of average values. Thus, if there are N partitions, the N average values are generated. The average value $A_i$ for the $i^{th}$ partition can be calculated as $$A_i = \frac{1}{\lambda_i - \lambda_{i-1}} \int_{\lambda_{i-1}}^{\lambda_i} I(\lambda)d\lambda$$

where $I(\lambda)$ is the average spectrum and $\lambda_{i-1}$ and $\lambda_i$ are the boundary wavelengths (with $\lambda_0 = \lambda_S$ and $\lambda_N = \lambda_E$).

The controller then selects the minimum value and the minimum value out of this group of average values, thus providing values MIN1 and MAX1, respectively.

In addition, the controller calculates an average value for the average reference spectrum. The average value can be calculated as the average of the group of averages values. For example, if there are N values in the group, the average AVE can be calculated as $$AVE = \frac{1}{N} \sum_{i=1}^{N} A_i$$

Alternatively, the average value can be calculated as the average value over the average reference spectrum. For example, AVE can be calculated as $$AVE = \frac{1}{\lambda_E - \lambda_S} \int_{\lambda_S}^{\lambda_E} I(\lambda)d\lambda$$

In addition, the controller determines the minimum and maximum values from the entire average reference spectrum (without using the average values calculated above). These minimum and maximum values can be labeled MIN2 and MAX2, respectively.

The values calculated above provide the boundaries for the intensity zones. For example, intensities below MIN2 provide a first zone, intensities between MIN2 and MIN1 provide a second zone, intensities between MIN1 and AVE provide a third zone, etc.

Having generated the partitions and the zones, the controller can next assign a code to each reference spectrum in the library. Each intensity zone is assigned a unique code value, e.g., an alphanumeric value. Thus, the multiple zones provide a group of code values.

For a particular reference spectrum, for each partition, the controller selects one code value of the group of code values. The code value can be selected based on a comparison of a value calculated from the portion of the spectrum within the partition to the boundaries of the zones. The code for the reference spectrum can be a concatenation of the code values for the partitions.

An example implementation to select the code values is as follows.

For a particular reference spectrum and a particular partition, a partition value is calculated based on the portion of the reference spectrum within the partition. For example, the average value of the spectrum within the particular partition (defined by the boundary wavelengths calculated for the average reference spectrum) is calculated. For example, the average value $B_i$ for the $i^{th}$ partition can be calculated as $$B_i = \frac{1}{\lambda_i - \lambda_{i-1}} \int_{\lambda_{i-1}}^{\lambda_i} R(\lambda)d\lambda$$

where $R(\lambda)$ is the reference spectrum and $\lambda_{i-1}$ and $\lambda_i$ are the boundary wavelengths (with $\lambda_0 = \lambda_S$ and $\lambda_N = \lambda_E$).

For each partition of the reference spectrum, the controller compares the average value, e.g., $B_i$, to the intensity zones 430. The controller determines which intensity zone the average value falls within, and the partition is assigned the code value associated with that zone. For example, if the average value is between MAX2 and MAX1, then the partition is assigned the code for that zone.

Once a code value has been calculated for each partition of the reference spectrum, the signature for the reference spectrum can be generated as a concatenation or an ordered sequence (in the same order as the partitions) of the code values for the partitions. Thus, if there are N partitions, the signature will be N code values long. In addition, if there are M intensity zones, then each code value in the signature will be one of M unique values. The signature can be expressed as S(i), which gives the code value associated with the $i^{th}$ partition.

For example, six intensity zones, then one of six letters can be assigned to each zone 430, and if the average spectrum is divided into 23 partitions, each reference spectrum in the library will receive a signature that is 23 letters long, with each letter being one of six possibilities.

Figure 7:
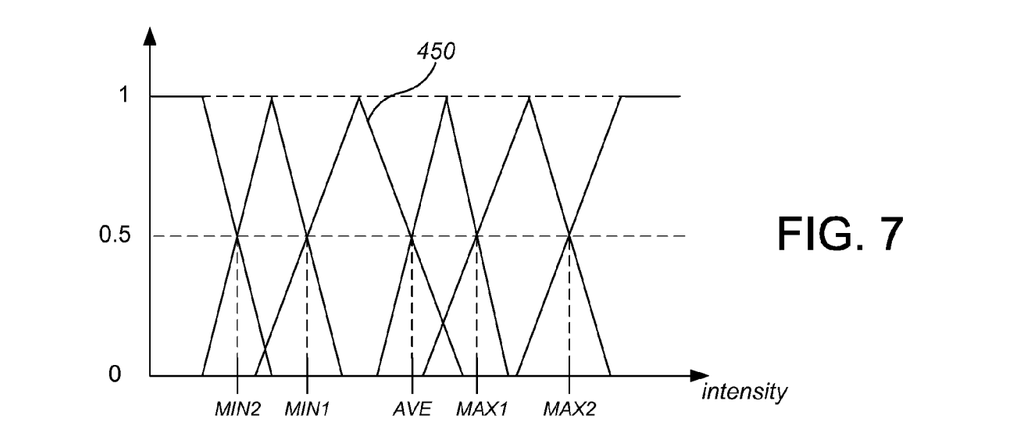
FIG. 7 illustrates a plurality of membership functions.

Referring to FIG. 7, a membership function 450 is defined for each intensity zone. Each membership function is a function of intensity (using the same scale as is used for the reference and measured spectra). Each membership function can vary between 0 and 1. Each membership function is associated with a unique one of the code values. In general, each membership function has a maximum value located in the intensity zone with which it is associated.

If there are M intensity zones, then there will be M membership functions. The membership functions can be expressed as $F_1(x)$, $F_2(x)$, ... $F_M(x)$, with x being an intensity value to be input into the function. Each membership function can be stored as a look-up table.

One implementation for the membership functions is as follows. Other than the membership functions for the uppermost and lowermost zones, each membership function can be a triangular function having a value of 0.5 at each intensity boundary of the zone and a value of 1 at the midpoint of the zone. For the uppermost and lowermost zones, the membership function can be a ramp function which is 0 at the midpoint of the adjacent zone, is a linear function from that midpoint and which passes through 0.5 at the boundary, and is 1 for values beyond where the linear function intersects 1.

Having defined the partitions, zone and the membership function, and assigned codes to the reference spectra, the reference spectrum that is the best match to a measured spectrum can be calculated.

For each partition, a partition value can be calculated based on the portion of the spectrum within the partition. The partition value is calculated using the same technique as is used to generate the partition values for the partitions of the average spectrum and reference spectra. For example, the average value of the measured spectrum within the particular partition (defined by the same boundary wavelengths calculated for the average reference spectrum) is calculated. For example, the average value $C_i$ for the $i^{th}$ partition can be calculated as $$C_i = \frac{1}{\lambda_i - \lambda_{i-1}} \int_{\lambda_{i-1}}^{\lambda_i} M(\lambda) d\lambda$$

where $M(\lambda)$ is the measured spectrum and $\lambda_{i-1}$ and $\lambda_i$ are the boundary wavelengths (with $\lambda_0 = \lambda_S$ and $\lambda_N = \lambda_E$). If there are N partitions, there will be N average values, e.g., $C_1$, $C_2$, ... $C_N$.

To compare a measured spectrum to a reference spectrum, for each partition, the code value associated with the particular partition is determined, and the membership function associated with that code value is determined. The value of the membership function at the partition value (e.g., the average value) for the partition of the measured spectrum is determined.

For example, using the terminology above, the membership value V of the $i^{th}$ partition is $$V_i = F_{S(i)}(C_i)$$

where S(i) is the code value of the signature of the reference spectrum for the $i^{th}$ partition.

If there are N partitions, this generates N membership values for the reference spectrum. This can be expressed as a group of membership values $V_1, V_2, \ldots V_N$. Since this is performed for each reference spectrum, a different group of membership values is generated for each reference spectrum, providing a plurality of groups of membership values.

The best matching reference spectrum can then be selected based on the plurality of groups of membership values.

In some implementations, a total value or average value of the membership values is calculated for each group, and the reference spectrum associated with the group with the largest total or average value is selected as the matching spectrum.

In some implementations, the controller determines the "next-to-minimum" membership value, i.e., the second-smallest membership value, for each group. The reference spectrum associated with the group having the largest next-to-minimum value is selected as the matching spectrum.

Using the algorithm described above, it is possible to increase the speed of recognizing incoming measured spectra, by a factor between approximately 13 and 48 as compared to a conventional sum-of-squared differences algorithm.

In another implementation, a "course-grained" comparison between the measured spectrum and the reference spectra is performed.

Initially, any reference spectrum is converted into a "coarse-grained" reference spectrum. In particular, the reference spectrum is divided into partitions of equal wavelength width. For example, each partition can be 50 Angstroms wide. For each partition, the average value of the reference spectrum within that partition is calculated. This provides the "coarse-grained" reference spectrum that is at lower wavelength resolution than the original reference spectrum. However, in some implementations, the reference spectra can be generated at the course-grained resolution, e.g., one intensity measurement per 50 Angstroms.

Similarly, each measured spectrum is divided into partitions of width equal to the wavelength width for the partitions of the reference spectrum. For example, each partition can be 2 to 220 wavelength values wide. For example, for the magnitude of the fractional error (|FE|) to be ≤1% after 20 seconds, the coarse-graining size (CGS) of the partitions can vary from 2 to 62 wavelength values. For |FE| to be ≤10% after 20 seconds, CGS can vary from 4 to 220 wavelength values. For each partition, the average value of the measured spectrum within that partition is calculated. This provides a "coarse-grained" measured spectrum that is at lower wavelength resolution than the original measured spectrum.

The difference between the "coarse-grained" measured spectrum and each "coarse-grained" reference spectrum can be determined using a sum of squared differences (SSD).

The "course-grained" reference spectrum with the least difference is determined, and the value associated with either the "course-grained" reference spectrum or the reference spectrum corresponding to the "course-grained" reference spectrum is determined.

As noted above, for each zone of each substrate, based on the sequence of measured spectra or that zone and substrate, the controller 190 can be programmed to generate a sequence of best matching spectra. A best matching reference spectrum can be determined by comparing a measured spectrum to the reference spectra from a particular library. In some implementations, the best matching reference spectrum can be determined by calculating, for each reference spectra, a sum of squared differences between the measured spectrum and the reference spectrum. The reference spectrum with the lowest sum of squared differences has the best fit.

Using this coarse-grained SSD algorithm, it is possible to increase the speed of recognizing incoming spectra by a factor of up to approximately 45, as compared to a regular SSD algorithm.

Once a matching reference spectrum has been selected, the characterizing value associated with the matching reference spectrum is identified.

Figure 8:
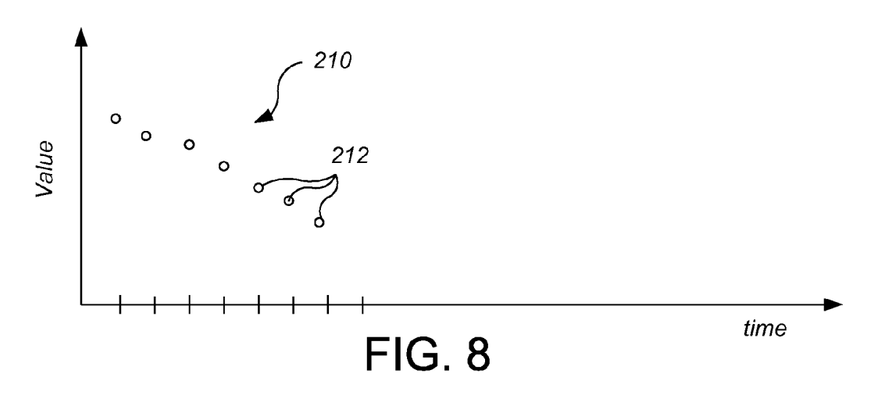
FIG. 8 illustrates a sequence of values generated by the in-situ optical monitoring system.

Referring to FIG. 8, which illustrates the results for only a single zone of a substrate, a time-varying sequence of characterizing values 212 is illustrated. This sequence of characterizing values can be termed a trace 210. In general, for a polishing system with a rotating platen, the trace 210 can include one, e.g., exactly one, characterizing value per sweep of the sensor of the optical monitoring system below the substrate. If multiple zones on a substrate are being monitored, then there can be one characterizing value per sweep per zone. Multiple measurements within a zone can be combined to generate a single characterizing value that is used for control of the endpoint and/or pressure. However, it is also possible for more than one characterizing value to be generated per sweep of the sensor.

Figure 9:
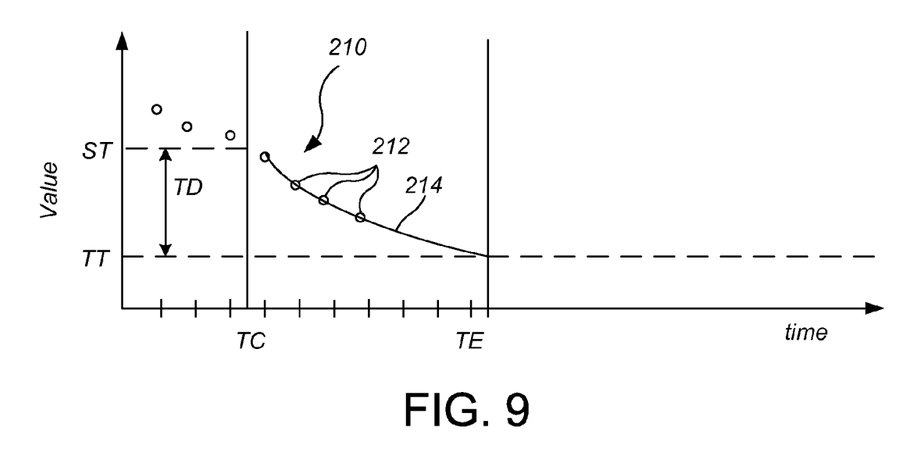
FIG. 9 illustrates a sequence of values having a user-input function fit to the sequence of values.

Prior to commencement of the polishing operation, the user or the equipment manufacturer can define a function 214 that will be fit to the time-varying sequence of characterizing values 212. For example, the function can be a polynomial function, e.g., a linear function. As shown in FIG. 9, the function 214 is fit to the sequence of characterizing values 212. Multiple techniques exist to fit generalized functions to data. For linear functions such as polynomials, a general linear least squares approach can be employed, e.g., as described in Chapter 15.4 of "Numerical Recipes in C".

Optionally, the function 214 can be fit to the characterizing values collected after time a TC. Characterizing values collected before the time TC can ignored when fitting the function to the sequence of characterizing values. For example, this can assist in elimination of noise in the measured spectra that can occur early in the polishing process, or it can remove spectra measured during polishing of another layer. Polishing can be halted at an endpoint time TE that the function 214 equals a target value TT.

It is possible to use generate a sequence of characterizing values for different zones of the substrate, and use the sequences from different zones to adjust the pressure applied in the chambers of the carrier head to provide more uniform polishing, e.g., using techniques described in U.S. application Ser. No. 13/096,777, incorporated herein by reference (in general, the position value can be substituted for the index value to use similar techniques). In some implementations, the sequence of values is used to adjust the polishing rate of one or more zones of a substrate, but another in-situ monitoring system or technique is used to detect the polishing endpoint.

In addition, although the discussion above assumes a rotating platen with a sensor of the in-situ monitoring system installed in the platen, system could be applicable to other types of relative motion between the sensor of the monitoring system and the substrate. For example, in some implementations, e.g., orbital motion, the sensor traverses different positions on the substrate, but does not cross the edge of the substrate. In such cases, measurements can be collected at a certain frequency, e.g., 1 Hz or more.

As used in the instant specification, the term substrate can include, for example, a product substrate (e.g., which includes multiple memory or processor dies), a test substrate, a bare substrate, and a gating substrate. The substrate can be at various stages of integrated circuit fabrication, e.g., the substrate can be a bare wafer, or it can include one or more deposited and/or patterned layers. The term substrate can include circular disks and rectangular sheets.

Embodiments of the invention and all of the functional operations described in this specification can be implemented in digital electronic circuitry, or in computer software, firmware, or hardware, including the structural means disclosed in this specification and structural equivalents thereof, or in combinations of them. Embodiments of the invention can be implemented as one or more computer program products, i.e., one or more computer programs tangibly embodied in a non-transitory machine readable storage media, for execution by, or to control the operation of, data processing apparatus, e.g., a programmable processor, a computer, or multiple processors or computers.

The above described polishing apparatus and methods can be applied in a variety of polishing systems. Either the polishing pad, or the carrier heads, or both can move to provide relative motion between the polishing surface and the substrate. For example, the platen may orbit rather than rotate. The polishing pad can be a circular (or some other shape) pad secured to the platen. Some aspects of the endpoint detection system may be applicable to linear polishing systems, e.g., where the polishing pad is a continuous or a reel-to-reel belt that moves linearly. The polishing layer can be a standard (for example, polyurethane with or without fillers) polishing material, a soft material, or a fixed-abrasive material. Terms of relative positioning are used; it should be understood that the polishing surface and substrate can be held in a vertical orientation or some other orientation.

Particular embodiments of the invention have been described. Other embodiments are within the scope of the following claims.

What is claimed is:

1. A method of controlling processing of a substrate, comprising:

processing a substrate;

measuring a spectrum reflected from the substrate with a spectrographic monitoring system to generate a measured spectrum;

partitioning the measured spectrum into a plurality of partitions, each partition spanning a different range of wavelengths of the measured spectrum;

for each partition of the plurality of partitions of the measured spectrum, computing a partition value based on the measured spectrum within the partition to generate a plurality of partition values;

for each reference spectrum signature of a plurality of reference spectrum signatures, determining a membership function for each partition of the plurality of partitions of the measured spectrum based on the reference spectrum signature;
for each partition of the plurality of partitions of the measured spectrum, computing a membership value based on the membership function for the partition and the partition value for the partition to generate a plurality of groups of membership values with each group of the plurality of groups associated with a reference spectrum signature;
selecting a best matching reference spectrum signature from the plurality of reference spectra signatures based on the plurality of groups of membership values;
determining a characterizing value associated with the best matching reference spectrum signature; and
adjusting processing of the substrate or a subsequent substrate based on the characterizing value.

2. The method of claim 1, wherein processing the substrate comprises polishing the substrate.

3. The method of claim 2, wherein measuring the spectrum comprises monitoring the substrate with an in-situ spectrographic monitoring system.

4. The method of claim 3, comprising generating a sequence of measured spectra, determining the characterizing value for each measured spectrum of the sequence of measured spectra to generate a sequence of characterizing values, and computing a polishing endpoint or an adjustment to a polishing parameter based on the sequence of characterizing values.

5. A computer program product, tangibly embodied in a non-transitory computer readable medium, comprising instructions for causing a processor to:
receive a measured spectrum of a substrate being processed from a spectrographic monitoring system;
partition the measured spectrum into a plurality of partitions, each partition spanning a different range of wavelengths of the measured spectrum;
for each partition of the plurality of partitions of the measured spectrum, compute a partition value based on the measured spectrum within the partition to generate a plurality of partition values;
for each reference spectrum signature of a plurality of reference spectrum signatures, determine a membership function for each partition of the plurality of partitions of the measured spectrum based on the reference spectrum signature
for each partition of the plurality of partitions of the measured spectrum, compute a membership value based on the membership function for the partition and the partition value for the partition to generate a plurality of groups of membership values with each group of the plurality of groups associated with a reference spectrum signature;
select a best matching reference spectrum signature from the plurality of reference spectra signatures based on the plurality of groups of membership values;
determine a characterizing value associated with the best matching reference spectrum signature; and
adjust processing of the substrate or a subsequent substrate based on the characterizing value.

6. The computer program product of claim 5, wherein each reference spectrum signature of the plurality of reference spectrum signatures includes a code value for each partition of the plurality of partitions of the reference spectrum, the code value associating the partition of the reference spectrum with a membership function.

7. The computer program product of claim 6, wherein the instructions to determine the membership function comprise instructions to use the membership function associated with the partition of the reference spectrum that corresponds to the partition of the measured spectrum.

8. The computer program product of claim 5, wherein the instructions to compute the partition value comprise instructions to compute an average value of the measured spectrum within the partition.

9. The computer program product of claim 5, wherein the instructions to select the best matching reference spectrum signature comprise instructions to, for each group, compute a total value of the membership values in the group to provide a plurality of total values, and select a reference spectrum signature associated with a group having the largest total value of the plurality of total values.

10. The computer program product of claim 5, wherein the instructions to select the best matching reference spectrum signature comprise instructions to, for each group, determining a second-lowest value of the group of values to provide a plurality of second-lowest values, and select a reference spectrum signature associated with a group having the largest second-lowest value of the plurality of second-lowest values.

11. The computer program product of claim 5, wherein each reference spectrum signature comprises a plurality of code values, each code value of the plurality of code values is associated with one of the plurality of partitions.

12. The computer program product of claim 11, wherein the instructions to determine the membership function for each partition comprise instructions to determine the code value in the reference spectrum signature associated with the partition, and determine the membership function associated with the code value.

13. The computer program product of claim 5, wherein the plurality of membership functions include a first triangular function having a first maximum value at a midpoint of a first intensity range and a second function having a second maximum value at a midpoint of a second intensity range, and wherein the first triangular function and the second triangular function having an equal value at a boundary between the first intensity range and the second intensity range.

14. The computer program product of claim 5, comprising instructions to compute the plurality of reference spectrum signatures based on a plurality of reference spectra.

15. The computer program product of claim 14, wherein the instructions to compute the plurality of reference spectrum signatures comprise instructions to compute an average reference spectrum, the average reference spectrum being an average of the plurality of reference spectra.

16. The computer program product of claim 15, comprising instructions to determine boundary wavelengths between the partitions based on the average reference spectrum.

17. The computer program product of claim 16, wherein the instructions to determine boundary wavelengths comprise instructions to compute wavelengths of a plurality of inflection points in the average reference spectrum, and compute boundary wavelengths that are a fraction of a distance between adjacent inflection points.

18. The computer program product of claim 15, comprising instructions to determine boundary intensities between a plurality of intensity zones based on the average reference spectrum.

19. The computer program product of claim 18, comprising instructions to compute a second partition value for each partition of the average reference spectrum, and determine boundary intensities includes selecting at least some of the second partition values.

20. The computer program product of claim 19, wherein the instructions to determine boundary intensities include instructions to calculate an average of the second partition values.

21. The computer program product of claim 18, comprising instructions to, for each partition of each reference spectrum, calculate a third partition value based on the reference spectrum within the partition, and select one of a plurality of unique code values based on comparing the third partition value to the intensity zones.

* * * * *